(12) United States Patent
Shorter et al.

(10) Patent No.: US 11,615,160 B2
(45) Date of Patent: Mar. 28, 2023

(54) DIGITAL LABEL MANAGEMENT

(71) Applicant: IQVIA Inc., Parsippany, NJ (US)

(72) Inventors: Gary Shorter, Durham, NC (US); Jaffershah Jahangeer, Bengaluru (IN)

(73) Assignee: IQVIA Inc., Parsippany, NJ (US)

( * ) Notice: Subject to any disclaimer, the term of this patent is extended or adjusted under 35 U.S.C. 154(b) by 66 days.

(21) Appl. No.: 17/242,770

(22) Filed: Apr. 28, 2021

(65) Prior Publication Data
US 2022/0350854 A1 Nov. 3, 2022

(51) Int. Cl.
G06F 16/955 (2019.01)
G16H 20/00 (2018.01)
G06K 7/14 (2006.01)
G06K 19/06 (2006.01)

(52) U.S. Cl.
CPC ....... *G06F 16/9554* (2019.01); *G06K 7/1417* (2013.01); *G06K 19/06009* (2013.01); *G16H 20/00* (2018.01)

(58) Field of Classification Search
CPC .. G06F 16/9554; G16H 20/00; G06K 7/1417; G06K 19/06009
See application file for complete search history.

(56) References Cited

U.S. PATENT DOCUMENTS

| | | | | |
|---|---|---|---|---|
| 2018/0349893 A1* | 12/2018 | Tsai | ........ | H04L 9/3239 |
| 2019/0303951 A1* | 10/2019 | Bakalis | .......... | G06K 7/12 |
| 2020/0117690 A1 | 4/2020 | Tran et al. | | |
| 2020/0265446 A1 | 8/2020 | Vargas | | |
| 2020/0279273 A1 | 9/2020 | Meszaros | | |
| 2021/0065110 A1 | 3/2021 | Li | | |
| 2021/0092185 A1 | 3/2021 | DeRosa-Grund | | |
| 2021/0105142 A1* | 4/2021 | Lee | .......... | H04L 9/0869 |
| 2022/0051238 A1 | 2/2022 | Zou | | |

FOREIGN PATENT DOCUMENTS

| | | |
|---|---|---|
| CN | 109461008 | 3/2019 |
| CN | 112712382 | 4/2021 |

OTHER PUBLICATIONS

International Search Report and Written Opinion in International Appln. No. PCT/US2022/071974, dated Jun. 27, 2022, 10 pages.

* cited by examiner

*Primary Examiner* — Azizul Choudhury
(74) *Attorney, Agent, or Firm* — Fish & Richardson P.C.

(57) ABSTRACT

Embodiments of the present disclosure provide a method for monitoring/tracking the lifecycle of a drug from build (e.g., as part of clinical trial development), to approval (e.g., regulatory), to in-market (e.g., distribution and safety information). The use of artificial intelligence (AI) and blockchain technology may enable the system to track the drug down to the prescription level and may support a digital label that can be updated as necessary based on such monitoring (e.g., that can be amended based on safety information detected while the drug is in market and warnings sent out upon amendment).

20 Claims, 7 Drawing Sheets

DIGITAL LABEL MANAGEMENT

TECHNICAL FIELD

Aspects of the present disclosure relate to digital label management using blockchain technology.

BACKGROUND

Digital labels may provide users of a product with information about the product. For example, some digital labels may comprise a quick response (QR) code which is a machine-readable optical label that contains information about the item to which it is attached. In practice, QR codes often contain data for a locator, identifier, or tracker that points to a website or application from which the information about the item can be viewed/retrieved.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

Current drug labels are subject to a number of issues. For example, current drug labels require identification and locating of the documents to be updated from the sponsors, ensuring multiple changes are properly sequenced to deliver submission accuracy, heavy manual forms updates and version controls which lengthens the process and is error prone, time delays and errors owing to scattered regulatory intelligence data needed for change, and the labor intensive nature of manual comparison of the before/after state of documents. In addition, current drug labels reflect handling of old compounds shifting from one company to another, account for companies buying biotech information which is not in clear electronic common technical document (eCTD) compliance, and account for the time taken to make an approval to drug label change, which can be many months and subsequently requires re-distribution of the label globally for new drug, while being unable to link back to old drug supply.

Smart label management refers to platforms that collect drug labels and other data in support of those labels. This includes blockchain, drug label digitalization, and drug label updates linked directly to QR codes for easy authorization and processing of necessary updates to drug label concerns. However, digital drug labels are not typically tracked from their originating source e.g., clinical trials through regulatory approval, and through to manufacture and supply/distribution of the drug. Digital labels are also not tracked through to any updates/data sources or through blockchain based on authorized individuals responsible for the digital label.

The present disclosure describes monitoring/tracking the lifecycle of a drug from build (e.g., as part of clinical trial development), to approval (e.g., regulatory), to in-market (e.g., distribution and safety information). The use of artificial intelligence (AI) and blockchain technology may enable the system to track the drug to the prescription level and may support a digital label that can be updated as necessary based on such monitoring (e.g., that can be amended based on safety information detected while the drug is in market and warnings sent out upon amendment).

A processing device may be utilized to generate label information comprising data about a product, the label information generated as part of a label creation process. The processing device may further generate, in a blockchain, a first blockchain entry corresponding to the label information and the label creation process, wherein the first blockchain entry is linked to the label information. The processing device may generate a label that is linked to a uniform resource locator (URL) of the blockchain, wherein in response to being scanned by a device, the label directs the device to the URL of the blockchain.

Figure 1:
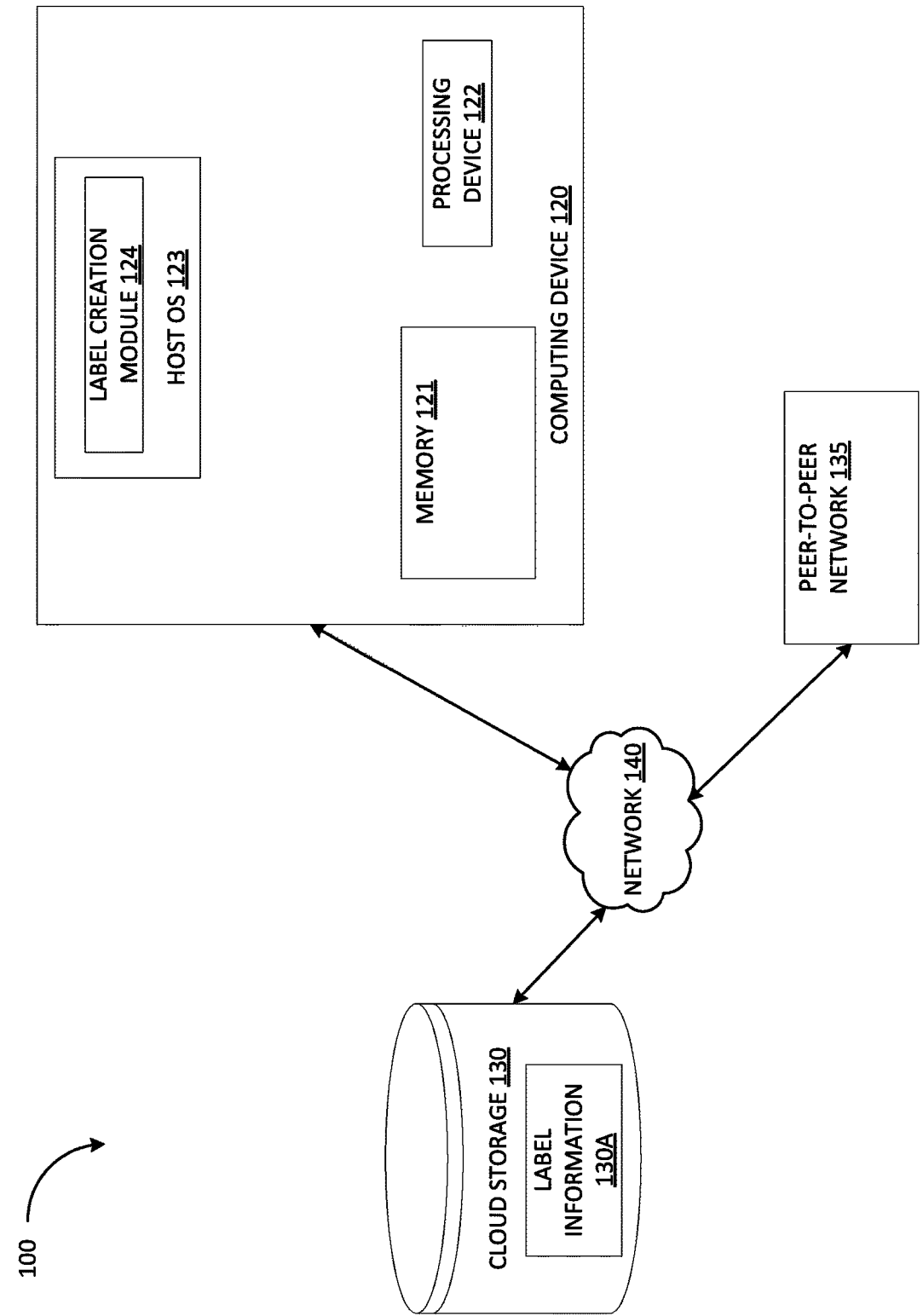
FIG. 1 is a block diagram that illustrates an example system, in accordance with some embodiments of the present disclosure.

FIG. 1 is a block diagram that illustrates an example system 100, for implementing a blockchain-based digital label management system. As illustrated in FIG. 1, the system 100 includes a computing device 120, a peer-to-peer (P2P) network 135, a cloud storage 130 and a network 140. The computing device 120, P2P network 135, and the cloud storage 130 may be coupled to each other (e.g., may be operatively coupled, communicatively coupled, may communicate data/messages with each other) via network 140. Network 140 may be a public network (e.g., the internet), a private network (e.g., a local area network (LAN) or wide area network (WAN)), or a combination thereof. In one embodiment, network 140 may include a wired or a wireless infrastructure, which may be provided by one or more wireless communications systems, such as a WiFi™ hotspot connected with the network 140 and/or a wireless carrier system that can be implemented using various data processing equipment, communication towers (e.g. cell towers), etc. The network 140 may carry communications (e.g., data, message, packets, frames, etc.) between computing device 120, P2P network 135, and cloud storage 130. The P2P network 135 may comprise a network of computing devices (not shown) on which a blockchain is implemented, as discussed in further detail herein. The computing device 120, each computing device of the P2P network 135, and cloud storage 130 may include hardware such as processing device 122 (e.g., processors, central processing units (CPUs)), memory 121 (e.g., random access memory (RAM), storage devices (e.g., hard-disk drive (HDD)), and solid-state drives (SSD), etc.), and other hardware devices (e.g., sound card, video card, etc.). A storage device may comprise a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices.

FIG. 1 and the other figures may use like reference numerals to identify like elements. A letter after a reference numeral, such as "110A," indicates that the text refers specifically to the element having that particular reference numeral. A reference numeral in the text without a following letter, such as "110," refers to any or all of the elements in the figures bearing that reference numeral.

The computing device 120 may be representative of a plurality of stakeholders (e.g., manufacturers of the drug) and actions taken by the computing device 120 as described herein may be representative of actions taken by one or more of the stakeholders during a label creation process or a label change process as discussed in further detail herein.

The computing device 120, each computing device of the P2P network 135, and cloud storage 130 may each comprise any suitable type of computing device or machine that has a programmable processor including, for example, server computers, desktop computers, laptop computers, tablet computers, smartphones, set-top boxes, etc. In some examples, the computing device 120, each computing device of the P2P network 135, and cloud storage 130 may comprise a single machine or may each include multiple interconnected machines (e.g., multiple servers configured in a cluster) that are all located at the same or different geographic region. The computing device 120, the P2P network 135, and cloud storage 130 may be implemented by a common entity/organization or may be implemented by different entities/organizations. For example, computing device 120 and the P2P network 135 may be operated by a first company/corporation and cloud storage 130 may be operated by a second company/corporation. The computing device 120, each computing device of the P2P network 135, and cloud storage 130 may each execute or include an operating system (OS) such as host OS 123 of computing device 120, as discussed in more detail below. The OSs of computing devices 120 and cloud storage 130 may manage the execution of other components (e.g., software, applications, etc.) and/or may manage access to the hardware (e.g., processors, memory, storage devices etc.) of the computing device.

Cloud storage 130 may further comprise a plurality of persistent storage devices that provide large-scale and high density data storage which may be virtualized into logical pools and provided to clients (e.g., over network 140) as e.g., object storage. Object storage is a computer data storage architecture that manages data as objects, where each object typically includes the data itself, a variable amount of metadata, and a globally unique identifier. In this way, clients can perform selective extraction and analysis of data. As shown in FIG. 1, cloud storage 130 may include label information 130A which may comprise a variety of data relevant to a drug and may be used to generate a label for the drug as discussed in further detail herein. Although embodiments of the present disclosure are described with respect to digital label management for a drug for exemplary purposes, they are not limited in this way and may be applied to management of a digital label applied to any appropriate product. As discussed in further detail herein, the label information 130A may be modified as the drug proceeds through its lifecycle which may include e.g., design/manufacture, regulatory approval, shipping/distribution, and in market, among other phases.

The label information 130A may initially comprise a variety of data related to the early phases of the drug's lifecycle (e.g., development and testing of the drug) such as drug composition, compound plans, clinical trial results, efficacy study results, expected therapeutic area (TA), target plan, safety test results, government entries, data relevant to eCTD regulatory filings, and data regarding which of a plurality of stakeholders (e.g., personnel involved in the design, manufacture, approval, and sale of the drug) were involved in obtaining each of the above data, for example. Data relevant to the eCTD filings may include the contents of the filings themselves, as well as details such as discussions surrounding the approval, reasons for regulatory approval, tests run, necessary/recommended warnings, and which regulatory personnel were involved in any of the above activities. The label information 130A may be generated by the plurality of stakeholders involved in the design, manufacture, and sale of the drug. For example, as epidemiology, medical/clinical, and biostatistics experts develop and test the drug, their work may be carried out on computing device 120 and stored on cloud storage 130 as their work progresses. In another example, as a regulatory affairs writer, submissions coordinator, and a local regulatory expert prepare reports and submissions for regulatory approval/receive regulatory approval and related information (e.g., warnings that the regulatory authority are requiring the stakeholders include on the label), this work may be carried out on computing device 120 and stored on cloud storage 130 as it progresses.

Computing device 120 may include a label creation module 124 which the computing device 120 may execute to perform one or more of the functions described herein. During a label approval process, the computing device 120 may collect the above mentioned data as well as other data relevant to the creation of a label for the drug and store the collected data as label information 130A. For example, a labelling expert, a label artwork creator, and a business development expert may generate artwork and packaging for the drug, which may be included as part of the label information 130A.

Figure 2:
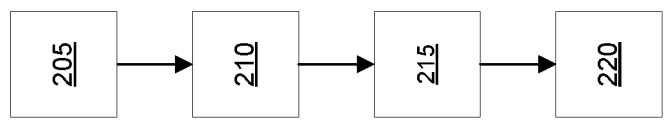
FIG. 2 is a diagram that illustrates a blockchain, in accordance with some embodiments of the present disclosure.
Figure 2:
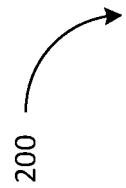

Referring also to FIG. 2, computing device 120 may generate a first block 205 in a blockchain 200 that corresponds to the drug. A blockchain may be considered as a distributed ledger, that is managed and implemented by a peer-to-peer (P2P) network wherein each device on the P2P network collectively adheres to a protocol for inter-node communication and validation of new blocks. Each block contains a cryptographic hash of the previous block, a timestamp, and transaction data. The cryptographic hash of the prior block links the 2 blocks, and linked blocks form a chain.

The computing device 120 may link the blockchain 200 (and more specifically, the first block 205) to the label information 130A. The blockchain 200 may be considered as a distributed ledger, that is managed and implemented by the P2P network 135, wherein each device on the P2P network 135 collectively adheres to a protocol for inter-node communication and validation of new blocks. Each block contains a cryptographic hash of the previous block, a timestamp, and transaction data (which may be hashed and encoded into e.g., a Merkle tree). The cryptographic hash of the prior block links the two blocks, and linked blocks form a chain. By design, a blockchain 200 may be resistant to modification of its data because once recorded, the data in any given block cannot be altered retroactively without alteration of all subsequent blocks. In some embodiments, the computing device 120 may be part of the P2P network 135 and may also implement the blockchain 200.

Figure 3:
FIG. 3 is a diagram of a digital label comprising a QR code, in accordance with some embodiments of the present disclosure.

The computing device 120 may then create a label that is linked to a URL of the blockchain 200. For example, the computing device 120 may generate label 300 comprising a digital QR code (as illustrated in FIG. 3) that is linked to the URL of the blockchain 200. The URL of the blockchain 200 may be a reference or pointer to the label information 130A, on the blockchain 200. The label 300 may be applied to bottles, cases, shipping containers, and other receptacles that may contain the drug during its lifecycle. In some embodiments, the label 300 may be applied to individual pills of the drug themselves. As the drug proceeds through its lifecycle, the label 300 may be scanned using any appropriate device (e.g., smart phone, tablet PC), resulting in the device (or another device in communication with the device) being redirected to the URL of the blockchain 200 where a user of the device may view the label information 130A. As the label information 130A (e.g., information underlying the label 300) is updated, subsequent scans of the label 300 may provide access to the updated information, as discussed in further detail herein.

In addition, as cases of the drug are shipped to various locations geographically, the label 300 may be scanned by various recipients (e.g., pharmacies, labs, government agencies), and each scan may trigger creation of a new block(s) 210 in the blockchain 200 indicating a new country, pharmacy, or region where the drug is being sold. More specifically, in response to a device corresponding to a pharmacy in a foreign country scanning the label 300, the device may be re-directed to the URL of the blockchain 200, and may also provide data indicating a location, name, entity type, and other relevant information about the pharmacy to the blockchain 200 which may trigger creation of a new block(s) 210 in the blockchain 200 where this information may be stored. In this way, the supply chain and distribution of the drug may be monitored via the blockchain 200 as well. In addition, once the drug is on the market, any of a number of in-market issues may be identified, requiring the label information 130A to be updated (e.g., with safety information such as new/different warnings, dosage directions etc.). As discussed in further detail herein, the label 300 may be used to allow users to view updates to the label information 130A.

Figure 4:
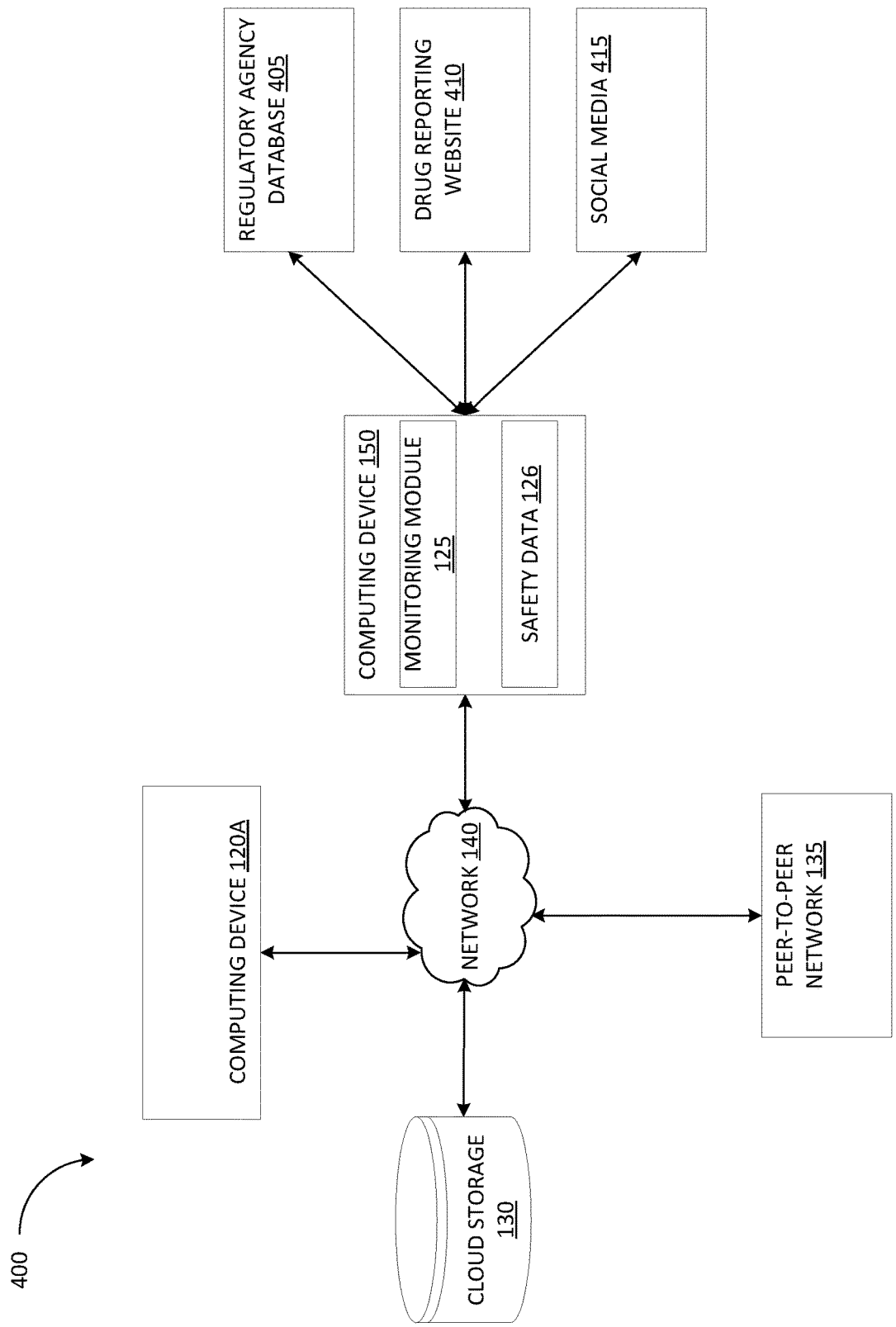
FIG. 4 is a block diagram that illustrates an example system, in accordance with some embodiments of the present disclosure.

FIG. 4 illustrates a system 400 which may be similar to the system 100 but may include computing device 150 (similar to other computing devices 120) which is executing a monitoring module 125 for monitoring in-market information including e.g., usage information and safety information, which may be reported through a variety of sources. Computing device 150 may represent stakeholders acting in a regulatory affairs capacity or a third party monitoring service monitoring for in-market information on behalf of stakeholders acting in a regulatory affairs capacity, for example.

Computing device 150 may monitor various data sources for safety information relevant to potential safety issues with the drug. For example, a lab may determine that certain users are experiencing allergic reactions to the drug and report this information to a regulatory agency. In another example, a doctor treating a patient using the drug may determine that the drug has made the patient anxious, and report this finding to the regulatory agency. Thus, computing device 150 may monitor a website and/or databases associated with the regulatory agency (e.g., regulatory agency database 405) for safety information relevant to potential issues with the drug. Computing device 150 may also monitor other sources for safety information relevant to potential safety issues with the drug, such as drug reporting website 410, which may be a website users of the drug can access to report safety information, and social media sources 415, where users of the drug can also report safety information, for example. Upon detecting such safety information, computing device 150 may compile and store the safety information as safety data 126, generate new block(s) 215 in the blockchain 200, and link the new block(s) 215 to the safety data 126. The computing device 150 may be required to periodically update the safety data 126 and push such updates to the block(s) 215 in the blockchain 200. The information included in the safety data 126 may include a source (e.g., regulatory agency database 405) the safety information was sourced from, an identity of the reporting entity (e.g., a lab or doctor testing/prescribing the drug), lab tests, testimonials, and/or reports involved in obtaining such safety information, and any other parties and their involvement in obtaining such safety information, for example. In this way, potential issues with the drug may be raised immediately with manufacturers, suppliers, and distributors etc. of the drug through the blockchain 200.

In response to the block(s) 215 being created or updated, the blockchain 200 may transmit a change event notification indicating the information in block 215 to the computing device 120, the purpose of which is to enable all stakeholders involved to assess the potential impact of the safety information (i.e., whether a change to the label information 130A underlying label 300 must be made). As the stakeholders of the drug view and analyze the safety data in block(s) 215, separate block(s) 220 may be created in blockchain 200 and linked to this viewership and analysis information. More specifically, as different stakeholders discuss and analyze the safety information, determine whether a change to the label information 130A needs to occur, come up with strategies, tests, and documentation regarding changes to the label information 130A, and approve such changes, the information regarding these activities (hereinafter referred to as "update information") may be added to label information 130A which may result in e.g., 'discussed', 'proposed', 'modified', 'approved', etc. versions of the label information 130A over time.

Because label information 130A is linked to the blockchain 200, such update information may automatically be recorded as a new block(s) 220 in the blockchain 200. As discussed above, computing device 120 may comprise a number of inter-connected computing devices and stakeholders involved in the above process do not need to be geographically located near each other. Individual stakeholders working remotely from each other may each view information from the blockchain 200 as necessary, and update the blockchain 200 by updating the label information 130A (e.g., adding newer versions to the label information 130A over time).

For example, certain stakeholders (e.g., via computing device 120) may access the safety data 126 from block 215 (e.g., as if they were accessing it from computing device 150) and prepare a label comparison table. More specifically, computing device 120 may retrieve current CCDS and confirm all regions/markets included and obtain the local label information (plus translate). Computing device 120 may formulate all this information into a comparison table for further assessment usage. Certain stakeholders may perform any necessary analysis and testing, and propose/confirm any CCDS changes required. Additionally, other stakeholders may obtain GLC Approval of CCDS changes, prepare required submissions to health authorities, and receive approval for the CCDS changes from the health authorities. Still other stakeholders may prepare and approve draft artwork, and generate an implementation plan including detailed implementation activities around regulatory live date and regional live dates. Finally, update information including information regarding each of the above actions and the stakeholders responsible for each is generated in order to update the label information 130A. The update information may be linked to new block(s) 220 created in the blockchain 200. In some embodiments, these actions may be grouped into one or more new blocks in the blockchain 200 (e.g., blocks 220A—220E—not shown). At this point, a user who scans the label 300 may be directed to the blockchain 200 which now includes the updates to label information 130A in the form of blocks 220.

In a similar manner, computing device 150 may also monitor the various data sources 405, 410, and 415 for usage information relevant to the use of the drug. This may include for example new uses of the drug, broader details concerning application of drug, added groups such as pediatric users or pregnant users etc. As new block(s) 215 are being created or updated with the usage information, the blockchain 200 may transmit a change event notification indicating the information in block 215 to the computing device 120, the purpose of which is to enable all stakeholders involved to assess the potential impact of the usage information (i.e., whether a change to the label information 130A underlying label 300 must be made). More specifically, as different stakeholders discuss and analyze the usage information, determine whether a change to the label information 130A needs to occur, come up with strategies, tests, and documentation regarding changes to the label information 130A, and approve such changes, the information regarding these activities ("update information") may be added to label information 130A. This may be important when stakeholders are e.g., trying to broaden the market and off-label use of the drug, and thus broader patient populations can lead to expanding upon/modifying the label 300 as well.

The blockchain 200 may also register approval of the updates to label information 130A by regulatory authorities (and any information pertinent thereto) within blocks 220. The blockchain 200 as a "smart contract" may have regulatory authorities in any country login, review the updates to label information 130A (that are linked via blockchain to the relevant label data version) and use the blockchain 200 to register their approval of that new label. Once the regulatory authority has registered approval, the label is available in real-time across the globe as a valid updated label. The approval by regulatory authorities may be linked to any downstream notifications needed on the blockchain 200 such as drug supply, pharmacy, other regulatory authorities, pharma company, doctors etc. This allows specifically for recognition of who is authorizing the drug and allows for authorities across the globe to consult and discuss the authorizations allowing for faster global review instead of individual one by one country review.

As can be seen, information relevant to the drug may be linked to label 300 digitally via blockchain 200. This allows for approval of content/information underlying label 300 to occur through blockchain 200. Once any changes to the data underlying the label 300 are authorized, such changes may be held on the blockchain 200 so that they cannot be altered. For example, the latest regulatory-agency approved communications regarding the drug may be made available through the label 300 (the QR code thereof). The distribution of the label 300 via QR code allows for a digital link between any instances of the drug and the drug's source. Updates to the label 300 are immediately connected to any receptacle carrying the drug and having the QR code and any entity, regardless of their location anywhere in the world may be able to obtain the latest information regarding the drug immediately from the label 300.

As discussed above, the P2P network 135 collectively adheres to a protocol for inter-node communication and validation of new blocks within the blockchain 200. In some embodiments, the blockchain 200 may utilize a protocol comprising one or more smart contracts that allow each update to the blockchain 200 to be saved as a transaction. A smart contract may be a computer program, a transaction protocol which is intended to automatically execute, control, document relevant events and actions according to certain conditions, etc. The execution and codified effects of a smart contract (e.g., the updating of information related to the safety of the drug) are strictly enforced and cannot be manipulated after a transaction with specific details is stored into the blockchain 200 (acting as e.g., a distributed ledger). This is because the actual execution of contracts is controlled and audited by the platform, not by any arbitrary server-side programs connecting to the platform. Because the blockchain 200 may be considered as an object oriented system, all entities (e.g., other systems/computing devices, label data, and program/protocol definitions) may be represented as objects, and smart contracts may be represented as operations on those objects. As a result, the data flows (e.g., program/protocol definitions) of the smart contract can be defined based on the label approval and label change processes, safety information reporting processes, and other processes discussed hereinabove.

The embodiments described herein provide numerous advantages. For example, the capability to deploy such a system on a secure cloud may provide global flexibility and reduced costs. The embodiments described herein also allow stakeholders to build out real-time end-to-end visibility of changes with a single source of truth (e.g., the blockchain providing an immutable ledger of activities). In addition, the digital label management methods herein may introduce automation to reduce cost and improve quality of updates to label information while allowing for more dynamic updates of label information (e.g., by introducing more formal feedback loops to learn from experience). The use of a QR code or similar technology within the label may allow for users anywhere in the world to link to real-time updates. The embodiments herein may also allow for additional search capability through digitization of documents which are all linked to the blockchain. The blockchain is linked to the downstream drug supply management so that stakeholders know where the drug is being distributed/sold at all times. Additional warnings are easy to apply through scan of the label on physical bottles, and if the label does not link to the proper authority's website, then the label (and thus the drug) may be determined to be fake/counterfeit.

Figure 5:
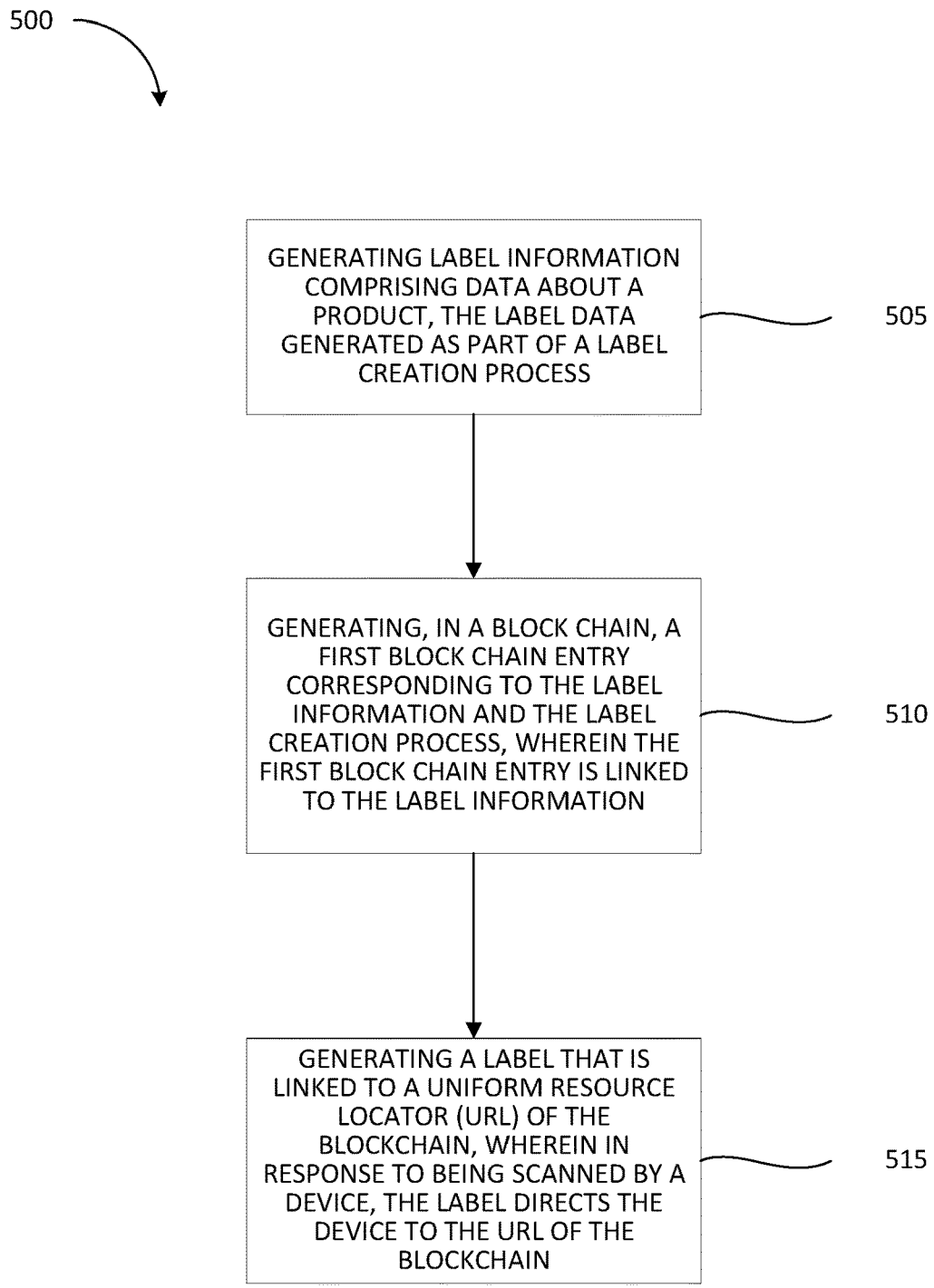
FIG. 5 is a flow diagram of a method for digital label management, in accordance with some embodiments of the present disclosure.

FIG. 5 is a flow diagram of a method 500 of managing a digital label, in accordance with some embodiments of the present disclosure. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 500 may be performed by one or more computing devices (e.g., computing device 120 and P2P network 135 illustrated in FIGS. 1 and 4).

Referring simultaneously to FIGS. 1 and 2, the method 500 begins at block 505, where computing device 120 may generate label information 130A comprising data about a drug, the label information 130A generated as part of a label creation process. The label information 130A may initially comprise a variety of data related to the early phases of the drug's lifecycle (e.g., development and testing of the drug) such as drug composition, compound plans, clinical trial results, efficacy study results, expected TA, target plan, safety test results, data relevant to electronic common technical document (eCTD) regulatory filings, government entries involved in the approval of the drug, and data regarding which of a plurality of stakeholders (e.g., personnel involved in the design, manufacture, approval, and sale of the drug) were involved in obtaining each of the above data, for example. Data relevant to the eCTD filings may include the contents of the filings themselves, as well as details such as discussions surrounding the approval, reasons for regulatory approval, tests run, necessary/recommended warnings, and which regulatory personnel were involved in any of the above activities. The label information 130A may be generated by the plurality of stakeholders involved in the design, manufacture, and sale of the drug. For example, as epidemiology, medical/clinical, and biostatistics experts develop and test the drug, their work may be carried out on computing device 120 and stored on cloud storage 130 as their work progresses. In another example, as a regulatory affairs writer, submissions coordinator, and a local regulatory expert prepare reports and submissions for regulatory approval/receive regulatory approval and related information (e.g., warnings that the regulatory authority are requiring the stakeholders include on the label), this work may be carried out on computing device 120 and stored on cloud storage 130 as it progresses.

Computing device 120 may include a label creation module 124 which the computing device 120 may execute to perform one or more of the functions described herein. During a label approval process, the computing device 120 may collect the above mentioned data as well as other data relevant to the creation of a label for the drug and store the collected data as label information 130A. For example, a labelling expert, a label artwork creator, and a business development expert may generate artwork and packaging for the drug, which may be included as part of the label information 130A.

Referring also to FIG. 2, at block 510, the computing device 120 may generate a first block 205 in a blockchain 200 that corresponds to the drug. The computing device 120 may link the blockchain 200 (and more specifically, the first block 205) to the label information 130A. The blockchain 200 may be considered as a distributed ledger, which is managed and implemented by the P2P network 135, wherein each device on the P2P network 135 collectively adheres to a protocol for inter-node communication and validation of new blocks. Each block contains a cryptographic hash of the previous block, a timestamp, and transaction data (which may be hashed and encoded into e.g., a Merkle tree). The cryptographic hash of the prior block links the 2 blocks, and linked blocks form a chain. By design, a blockchain 200 may be resistant to modification of its data because once recorded, the data in any given block cannot be altered retroactively without alteration of all subsequent blocks. In some embodiments, the computing device 120 may be part of the P2P network 135 and may also implement the blockchain 200.

At block 515, the computing device 120 may then create a label that is linked to a URL of the blockchain 200. For example, the computing device 120 may generate label 300 comprising a digital QR code (as illustrated in FIG. 3) that is linked to the URL of the blockchain 200. The label 300 may be applied to bottles, cases, shipping containers, and other receptacles that may contain the drug during its lifecycle. As the drug proceeds through its lifecycle, the label 300 may be scanned using any appropriate device (e.g., smart phone, tablet PC), resulting in the device (or another device in communication with the device) being redirected to the URL of the blockchain 200 where a user of the device may view the label information 130A. As the label information 130A (e.g., information underlying the label 300) is updated, subsequent scans of the label 300 may provide access to the updated information, as discussed in further detail herein.

Figure 6:
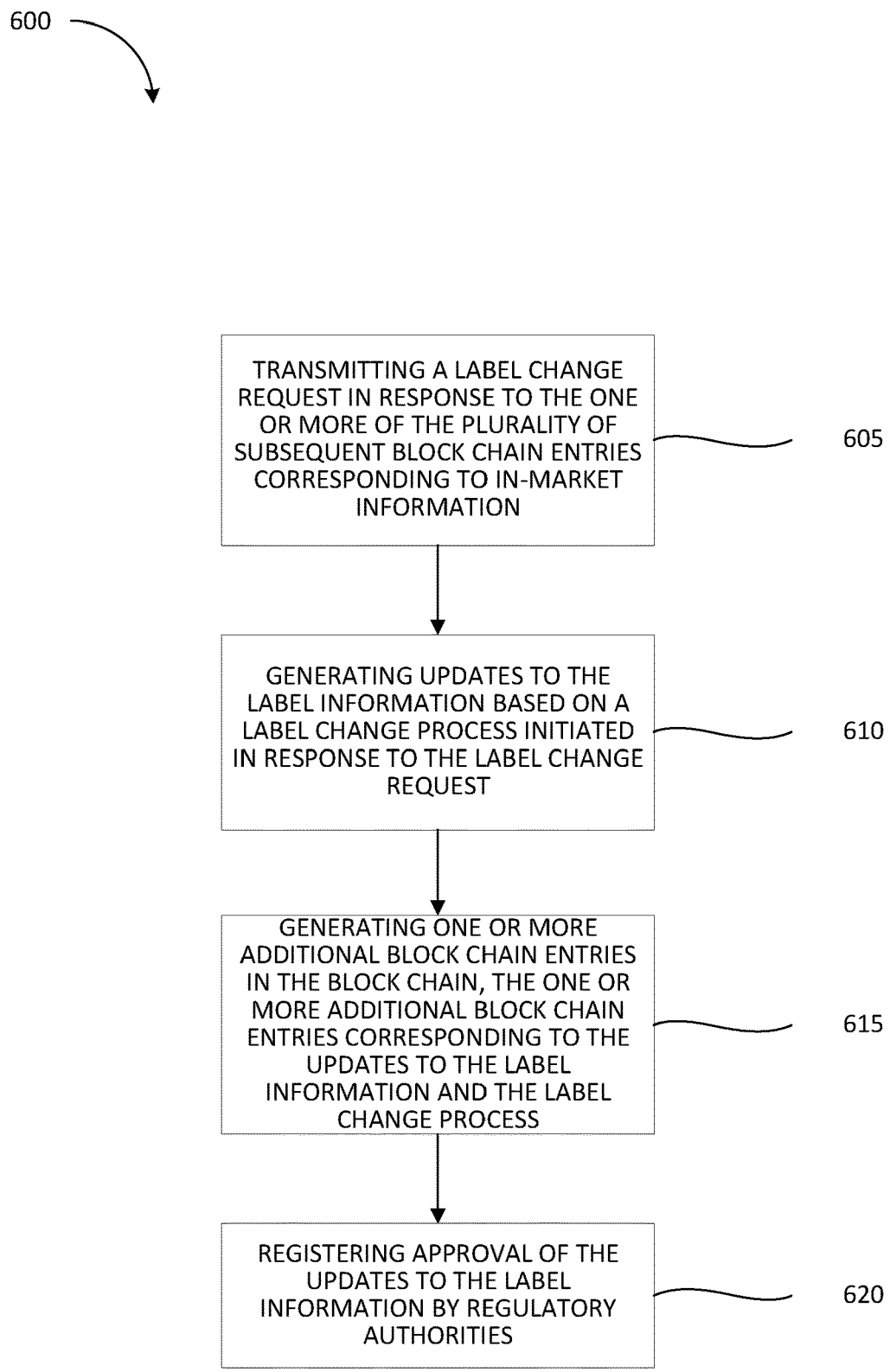
FIG. 6 is a flow diagram of a method for updating the underlying data of a digital label, in accordance with some embodiments of the present disclosure.

FIG. 6 is a flow diagram of a method 600 for updating the information underlying a digital label, in accordance with some embodiments of the present disclosure. Method 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 600 may be performed by one or more computing devices (e.g., computing device 120 and P2P network 135 illustrated in FIGS. 1 and 4).

Computing device 150 may monitor various data sources for in-market information relating to the drug. For example, a lab may determine that certain users are experiencing allergic reactions to the drug and report this information to a regulatory agency. In another example, a doctor treating a patient using the drug may determine that the drug has made the patient anxious, and report this finding to the regulatory agency. Thus, computing device 150 may monitor a website and/or databases associated with the regulatory agency (e.g., regulatory agency database 405) for safety information relevant to potential issues with the drug. Computing device 150 may also monitor other sources for safety information relevant to potential safety issues with the drug, such as drug reporting website 410, which may be a website users of the drug can access to report safety information, and social media sources 415, where users of the drug can also report safety information, for example. Upon detecting such safety information, computing device 150 may compile and store the safety information as safety data 126, generate new block(s) 215 in the blockchain 200, and link the new block(s) 215 to the safety data 126. The computing device 150 may be required to periodically update the safety data 126 and push such updates to the block(s) 215 in the blockchain 200. The information included in the safety data 126 may include a source (e.g., regulatory agency database 405) the safety information was sourced from, an identity of the reporting entity (e.g., a lab or doctor testing/prescribing the drug), lab tests, testimonials, and/or reports involved in obtaining such safety information, and any other parties and their involvement in obtaining such safety information, for example. In this way, potential issues with the drug may be raised immediately with manufacturers, suppliers, and distributors etc. of the drug through the blockchain 200.

In response to the block(s) 215 being created or updated, at block 605, the blockchain 200 may transmit a change event notification indicating the information in block 215 to the computing device 120, the purpose of which is to enable all stakeholders involved to assess the potential impact of the safety information (i.e., whether a change to the label information 130A underlying label 300 must be made). At block 610, as different stakeholders discuss and analyze the safety information, determine whether a change to the label information 130A needs to occur, come up with strategies, tests, and documentation regarding changes to the label information 130A, and approve such changes, the information regarding these activities (hereinafter referred to as "update information") may be added to label information 130A.

For example, certain stakeholders (e.g., via computing device 120) may access the safety data 126 from block 215 (e.g., as if they were accessing it from computing device 150) and prepare a label comparison table. More specifically, computing device 120 may retrieve current CCDS and confirm all regions/markets included and obtain the local label information (plus translate). Computing device 120 may formulate all this information into a comparison table for further assessment usage. Certain stakeholders may perform any necessary analysis and testing, and propose/confirm any CCDS changes required. Additionally, other stakeholders may obtain GLC Approval of CCDS changes, prepare required submissions to health authorities, and receive approval for the CCDS changes from the health authorities. Still other stakeholders may prepare and approve draft artwork, and generate an implementation plan including detailed implementation activities around regulatory live date and regional live dates. Finally, update information including information regarding each of the above actions and the stakeholders responsible for each is generated in order to update the label information 130A.

In a similar manner, computing device 150 may also monitor the various data sources 405, 410, and 415 for usage information relevant to the use of the drug. This may include for example new uses of the drug, broader details concerning application of drug, added groups such as paediatric users or pregnant users etc. As new block(s) 215 are being created or updated with the usage information, the blockchain 200 may transmit a change event notification indicating the information in block 215 to the computing device 120, the purpose of which is to enable all stakeholders involved to assess the potential impact of the usage information (i.e., whether a change to the label information 130A underlying label 300 must be made). More specifically, as different stakeholders discuss and analyze the usage information, determine whether a change to the label information 130A needs to occur, come up with strategies, tests, and documentation regarding changes to the label information 130A, and approve such changes, the information regarding these activities ("update information") may be added to label information 130A. This may be important when stakeholders are e.g., trying to broaden the market and off-label use of the drug, and thus broader patient populations can lead to expanding upon/modifying the label 300 as well.

At block 615, the update information may be linked to new block(s) 220 created in the blockchain 200. In some embodiments, these actions may be grouped into one or more new blocks in the blockchain 200 (e.g., blocks 220A—220E—not shown). At this point, a user who scans the label 300 may be directed to the blockchain 200 which now includes the updates to label information 130A in the form of blocks 220. Because label information 130A is linked to the blockchain 200, such update information may automatically be recorded as a new block(s) 220 in the blockchain 200. As discussed above, computing device 120 may comprise a number of inter-connected computing devices and stakeholders involved in the above process do not need to be geographically located near each other. Individual stakeholders working remotely from each other may each view information from the blockchain 200 as necessary, and update the blockchain 200 by updating the label information 130A.

At block 620, the blockchain 200 may also register approval of the updates to label information 130A by regulatory authorities (and any information pertinent thereto) within blocks 220. The blockchain 200 as a "smart contract" may have regulatory authorities in any country login, review the updates to label information 130A (that are linked via blockchain to the relevant label data version) and use the blockchain 200 to register their approval of that new label. Once the regulatory authority has registered approval, the label is available in real-time across the globe as a valid updated label. The approval by regulatory authorities may be linked to any downstream notifications needed on the blockchain 200 such as drug supply, pharmacy, other regulatory authorities, pharma company, doctors etc. This allows specifically for recognition of who is authorizing the drug and allows for authorities across the globe to consult and discuss the authorizations allowing for faster global review instead of individual one by one country review.

Figure 7:
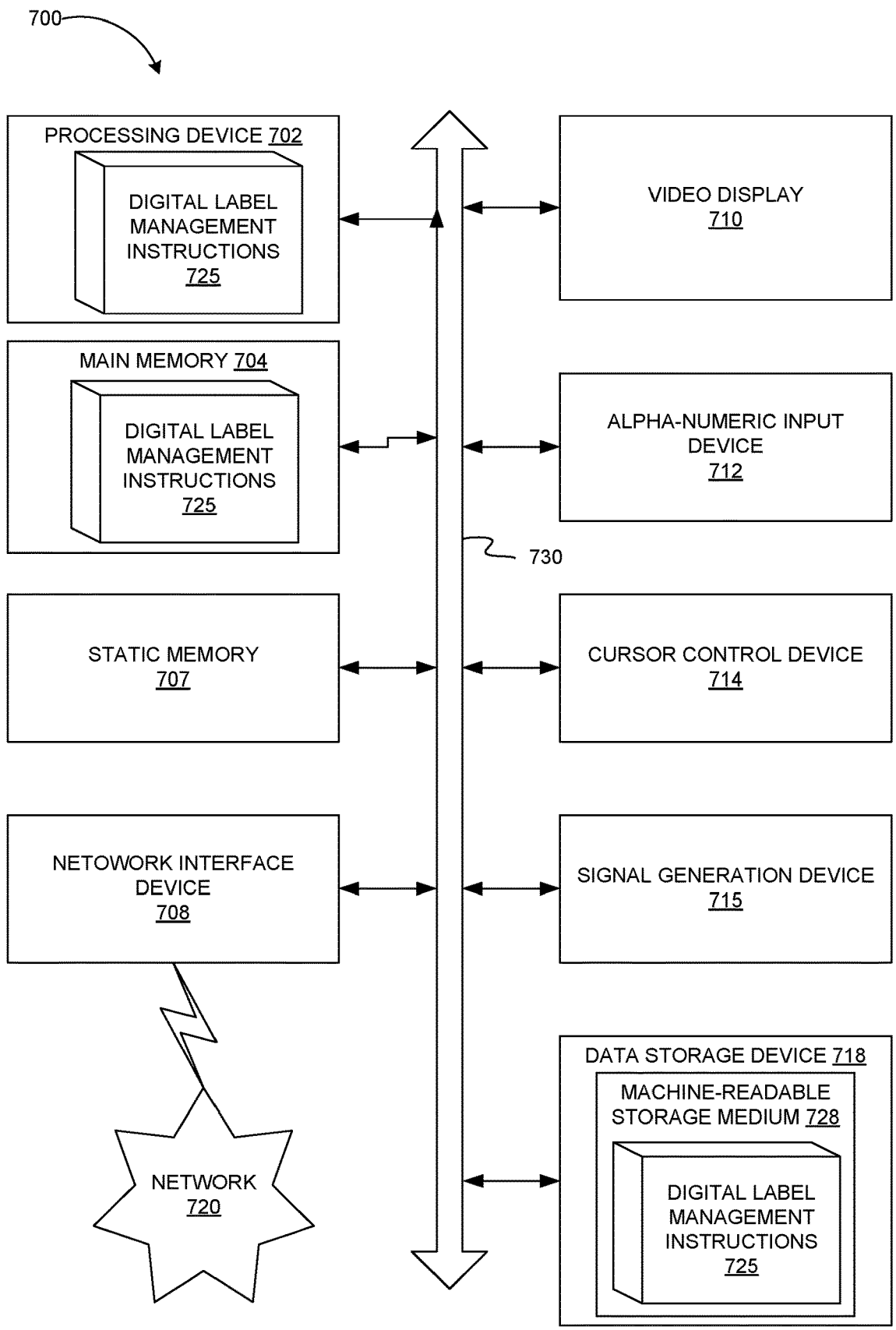
FIG. 7 is a block diagram of an example computing device that may perform one or more of the operations described herein, in accordance with some embodiments of the present disclosure.

FIG. 7 illustrates a diagrammatic representation of a machine in the example form of a computer system 700 within which a set of instructions, for causing the machine to perform any one or more of the methodologies discussed herein for digital label management. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 700 may be representative of a server.

The exemplary computer system 700 includes a processing device 702, a main memory 704 (e.g., read-only memory (ROM), flash memory, dynamic random access memory (DRAM), a static memory 706 (e.g., flash memory, static random access memory (SRAM), etc.), and a data storage device 718, which communicate with each other via a bus 730. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 716 (e.g., a speaker). In one embodiment, video display unit 710, alphanumeric input device 712, and cursor control device 714 may be combined into a single component or device (e.g., an LCD touch screen).

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute peer network influence measurement instructions 725, for performing the operations and steps discussed herein.

The data storage device 718 may include a machine-readable storage medium 728, on which is stored one or more sets of digital label management instructions 725 (e.g., software) embodying any one or more of the methodologies of functions described herein. The digital label management instructions 725 may also reside, completely or at least partially, within the main memory 704 or within the processing device 702 during execution thereof by the computer system 700; the main memory 704 and the processing device 702 also constituting machine-readable storage media. The digital label management instructions 725 may further be transmitted or received over a network 720 via the network interface device 708.

The machine-readable storage medium 728 may also be used to store instructions to provide digital label management, as described herein. While the machine-readable storage medium 728 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:
1. A method comprising:
   generating label information comprising data about a product, the label information generated as part of a label creation process;
   generating, in a blockchain, a first blockchain entry corresponding to the label information and the label cre- ation process, wherein the first blockchain entry is linked to the label information;

generating, by a processing device, a label that is linked to a uniform resource locator (URL) of the blockchain, wherein in response to the label being scanned by a device, the label directs the device to the URL of the blockchain;

in response to detection of a market issue related to the product, generating, in the blockchain, a second blockchain entry that stores data indicative of the detected market issue related to the product;

providing, by the processing device, a notification indicating the detected market issue for output;

in response to providing the notification indicating the detected market issue, receiving, by the processing device, information indicative of one or more adjustments to the label information in the blockchain; and generating, in the blockchain, a third blockchain entry that stores the received information indicative of the one or more adjustments to the label.

2. The method of claim 1, further comprising:
generating, in the blockchain, a plurality of subsequent blockchain entries corresponding to information about the product after market introduction.

3. The method of claim 2, wherein one or more of the plurality of subsequent blockchain entries correspond to distribution information of the product obtained in response to the label being scanned by one or more distribution entities.

4. The method of claim 2, wherein one or more of the plurality of subsequent blockchain entries correspond to safety information about the product obtained from an in-market information monitor.

5. The method of claim 4, further comprising:
transmitting a label change request in response to the one or more of the plurality of subsequent blockchain entries corresponding to safety information;
generating updates to the label information based on a label change process initiated in response to the label change request; and
generating one or more additional blockchain entries in the blockchain, the one or more additional blockchain entries corresponding to the updates to the label information and the label change process.

6. The method of claim 1, wherein the blockchain implements a protocol comprising one or more smart contracts.

7. The method of claim 1, wherein the label comprises a quick response (QR) code.

8. A system comprising:
one or more computers and one or more storage devices storing instructions that are operable, when executed by the one or more computers, to cause the one or more computers to perform operations comprising:
generating label information comprising data about a product, the label information generated as part of a label creation process;
generating, in a blockchain, a first blockchain entry corresponding to the label information and the label creation process, wherein the first blockchain entry is linked to the label information;
generating, by a processing device, a label that is linked to a uniform resource locator (URL) of the blockchain, wherein in response to the label to being scanned by a device, the label directs the device to the URL of the blockchain;
in response to detection of a market issue related to the product, generating, in the blockchain, a second blockchain entry that stores data indicative of the detected market issue related to the product;
providing, by the processing device, a notification indicating the detected market issue for output;
in response to providing the notification indicating the detected market issue, receiving, by the processing device, information indicative of one or more adjustments to the label information in the blockchain; and
generating, in the blockchain, a third blockchain entry that stores the received information indicative of the one or more adjustments to the label.

9. The system of claim 8, further comprising:
generating, in the blockchain, a plurality of subsequent blockchain entries corresponding to information about the product after market introduction.

10. The system of claim 9, wherein one or more of the plurality of subsequent blockchain entries correspond to distribution information of the product obtained in response to the label being scanned by one or more distribution entities.

11. The system of claim 9, wherein one or more of the plurality of subsequent blockchain entries correspond to safety information about the product obtained from an in-market information monitor.

12. The system of claim 11, wherein the processing device is further to:
transmitting a label change request in response to the one or more of the plurality of subsequent blockchain entries corresponding to safety information;
generating updates to the label information based on a label change process initiated in response to the label change request; and
generating one or more additional blockchain entries in the blockchain, the one or more additional blockchain entries corresponding to the updates to the label information and the label change process.

13. The system of claim 8, wherein the blockchain implements a protocol comprising one or more smart contracts.

14. The system of claim 8, wherein the label comprises a quick response (QR) code.

15. A non-transitory computer-readable medium storing software comprising instructions executable by one or more computers which, upon such execution, cause the one or more computers to perform operations comprising:
generating label information comprising data about a product, the label information generated as part of a label creation process;
generating, in a blockchain, a first blockchain entry corresponding to the label information and the label creation process, wherein the first blockchain entry is linked to the label information;
generating, by a processing device, a label that is linked to a uniform resource locator (URL) of the blockchain, wherein in response to the label being scanned by a device, the label directs the device to the URL of the blockchain;
in response to detection of a market issue related to the product, generating, in the blockchain, a second blockchain entry that stores data indicative of the detected market issue related to the product;
providing, by the processing device, a notification indicating the detected market issue for output;
in response to providing the notification indicating the detected market issue, receiving, by the processing device, information indicative of one or more adjustments to the label information in the blockchain; and generating, in the blockchain, a third blockchain entry that stores the received information indicative of the one or more adjustments to the label.

16. The non-transitory computer-readable medium of claim 15, further comprising:
generating, in the blockchain, a plurality of subsequent blockchain entries corresponding to information about the product after market introduction.

17. The non-transitory computer-readable medium of claim 16, wherein one or more of the plurality of subsequent blockchain entries correspond to distribution information of the product obtained in response to the label being scanned by one or more distribution entities.

18. The non-transitory computer-readable medium of claim 16, wherein one or more of the plurality of subsequent blockchain entries correspond to safety information about the product obtained from an in-market information monitor.

19. The non-transitory computer-readable medium of claim 18, further comprising:
transmitting a label change request in response to the one or more of the plurality of subsequent blockchain entries corresponding to safety information;
generating updates to the label information based on a label change process initiated in response to the label change request; and
generating one or more additional blockchain entries in the blockchain, the one or more additional blockchain entries corresponding to the updates to the label information and the label change process.

20. The non-transitory computer-readable medium of claim 15, wherein the blockchain implements a protocol comprising one or more smart contracts.

* * * * *